(12) United States Patent
Rising et al.

(10) Patent No.: US 8,679,775 B2
(45) Date of Patent: Mar. 25, 2014

(54) INFRARED MEASUREMENT FOR THE RAPID ENUMERATION OF MICROBIAL CONCENTRATIONS

(75) Inventors: Peter E. Rising, Brightwaters, NY (US); Brian H. Rutledge, Eldersburg, MD (US); James L. Robinson, Macon, GA (US)

(73) Assignee: Industrial Municipal Equipment, Inc., Eldersburg, MA (US)

( * ) Notice: Subject to any disclaimer, the term of this patent is extended or adjusted under 35 U.S.C. 154(b) by 1464 days.

(21) Appl. No.: 11/666,027

(22) PCT Filed: Oct. 21, 2005

(86) PCT No.: PCT/US2005/038041
§ 371 (c)(1),
(2), (4) Date: Aug. 27, 2007

(87) PCT Pub. No.: WO2006/047336
PCT Pub. Date: May 4, 2006

(65) Prior Publication Data
US 2008/0113403 A1  May 15, 2008

Related U.S. Application Data

(60) Provisional application No. 60/621,333, filed on Oct. 21, 2004, provisional application No. 60/668,328, filed on Apr. 4, 2005.

(51) Int. Cl.
*C12Q 1/02*  (2006.01)
(52) U.S. Cl.
USPC ............................................ 435/29; 435/34

(58) Field of Classification Search
USPC ........................................................ 435/29, 34
See application file for complete search history.

(56) References Cited

U.S. PATENT DOCUMENTS

| | | | |
|---|---|---|---|
| 5,422,720 A | 6/1995 | Berndt | |
| 5,482,842 A | 1/1996 | Berndt | |
| 6,768,549 B1 | 7/2004 | Pfeifer | |
| 2003/0203422 A1 | 10/2003 | Edberg | |

FOREIGN PATENT DOCUMENTS

| | | |
|---|---|---|
| DE | 3419327 | 11/1985 |
| FR | 2097329 | 3/1972 |
| GB | 1435582 | 5/1976 |

OTHER PUBLICATIONS

Waechter-Kristensen et al. "Comparison of sole carbon source profiles monitored at two different wavelengths", J of Microbiological Methods, 1998, 34:17-21.*
European search report dated Apr. 11, 2012.

* cited by examiner

*Primary Examiner* — Bin Shen
(74) *Attorney, Agent, or Firm* — F. Chau & Associates, LLC

(57) ABSTRACT

A method for testing for presence of a microbe in a sample includes measuring an instantaneous transmission rate of two or more wavelengths through the sample (1403), providing predetermined transmission rates corresponding to positive or negative samples for the presence of the microbe for each of the two or more wavelengths, and determining a probability of the presence of the microbe based on the instantaneous transmission rate for each of the two or more wavelengths through the sample by comparing the instantaneous transmission rate to the predetermined transmission rates (1404).

9 Claims, 13 Drawing Sheets

TRUE BIOLOGIC POSITIVE SAMPLE

FALSE POSITIVE BIOLOGIC SAMPLE

INFRARED MEASUREMENT FOR THE RAPID ENUMERATION OF MICROBIAL CONCENTRATIONS

This application claims the priority of U.S. Provisional Application No. 60/621,333, filed on Oct. 21, 2004, and U.S. Provisional Application No. 60/668,328, filed on Apr. 4, 2005, in the United States Patent and Trademark Office, the disclosures of which is incorporated herein in its entirety by reference.

BACKGROUND OF THE INVENTION

1. Field of the Invention

The present invention relates to chemical assays, and more particularly to a system and method for infrared measurement of microbiological activity.

2. Discussion of Related Art

Biologists use indicator chemicals to enhance and accelerate the identification of microbial colonies when attempting to determine microbial concentration levels for specific samples being tested. One of the problems identified with using such indicator chemicals is that they can have a reaction to non-microbial stimuli such as treatment chemicals and drugs. This is particularly true for broad-spectrum microbial indicators such as TTC and other ORP indicator chemicals that are used in the enumeration of aerobic microbes present in a sample. This chemical positive reaction is particularly true of but not limited to microbial tests that use an aqueous testing matrix. The presence of reductive chemicals causes the TTC indicator to turn the normal end of test red hue whether microbes are present or not. This situation may lead to a false positive for microbes test result or an erroneous microbial concentration level determination. In some microbial testing applications, such as the culturing of urine samples, a false position may result from various types of antioxidant therapy (e.g., vitamin C and etc.) or certain types of antibiotics. The elimination of chemical positive results that are not biologically positive has a positive effect upon the microbial test analysis, as test results are not delayed by secondary tests. The occurrence of such chemical positive/biologic negative test results can vary greatly and in an unpredictable or known manner from one test application to another test application. Similar undesired test variation can occur from one sample to another sample with an application because of reasons of sample environment change. As an example for human urine testing a person providing a urine sample who is on antioxidant therapy can provide a chemically positive test sample which is not biologic positive in the morning period but provide a chemically negative and biologically negative in the afternoon. This occurs when the urine residuals of oxidant materials are high based upon the amount of antioxidant taken, time of dose and relative chemical health of the individual at the time of sampling. Similar difficulty can occur with samples taken from closed loop water-cooling systems. This result is particularly true for medical applications where the application of medicinal steps is made faster and fewer cases of antibiotic over dosing occur.

The enumeration and speciation of microbial populations may include the use various kinds of media plates, slants and or agar swabs. These analysis techniques do not yield, by themselves, the growth phase of a microbial population. Known techniques merely determine microbial presence, level and species. If the biologic analyst wishes to determine the growth phase of a microbial population at sampling time, a series of time consuming tests and calculations need to be performed with the specific intent of estimating the growth phase of the microbial population. Growth phase of microbial populations is an important factor in the proper analysis and control of many microbial populations.

Methods for speciation in samples having mixed microbe populations can be difficult. For example, in a mixed population, attempts to determine a particular species that may be the cause of an infection, e.g., a species having a highest concentration, are complicated by detection techniques. To determine the species in the sample, the sample is plated and grown on a media. Thus, all species in the sample are provided the opportunity for growth. Therefore, it can be difficult to determine a culprit of the infection.

Therefore, a need exists for a system and method of reducing chemical false positive results and determining microbial growth phase (log vs. lag) of detected microbial populations.

SUMMARY OF THE INVENTION

A test for the presence of microbes is performed. The test includes measurements for a time-to-concentration for biological growth combined with an infrared measurement over time. The combination of time-to-concentration and infrared measurements decreases false positive results. Further the test may be performed in a time frame competitive with chemical indicators.

Each sample functions as its own standard, no control is needed. By measuring changes in a parameter, such as turbidity or color, no control is needed.

Curves for two or more spectral wavelengths are used to identify a microbial species according to a transmission rate through a sample. Having a catalog of spectral change, e.g., the change in transmission rate over time, by microbial species, enhances the ability to determine the degree of log phase and species of a microbial population. A spectral match in the change of slope of each monitored wavelength and relative locus of slope changes for various spectral wavelengths being monitored designates microbial species.

According to an embodiment of the present disclosure, a method for testing for presence of a microbe in a sample includes measuring, simultaneously, transmissions of two or more wavelengths of light through the sample over time, measuring a time-to-concentration for biological growth in the sample for each of the two or more wavelength transmissions, and determining the presence of the microbe based on a combination of the time-to-concentration measurement for each of the two or more wavelengths.

The sample functions as its own standard, no control is used.

The two or more wavelengths are an infrared wavelength and a visible wavelength.

The method includes comparing a change in transmission rate for each of the two or more wavelengths over time to a catalog of spectral change, and determining a spectral match in the change of slope of each monitored wavelength and relative locus of slope changes for various spectral wavelengths being monitored designates a microbial species.

According to an embodiment of the present disclosure, a method for testing for presence of a microbe in a sample includes measuring an instantaneous transmission rate of two or more wavelengths through the sample, providing predetermined transmission rates corresponding to positive or negative samples for the presence of the microbe for each of the two or more wavelengths, and determining a probability of the presence of the microbe based on the instantaneous transmission rate for each of the two or more wavelengths through the sample by comparing the instantaneous transmission rate to the predetermined transmission rates.

Each of the predetermined transmission rates is associated with a known confidence level.

The probability of the presence of the microbe is compared to a predetermined threshold, wherein upon determining the sample has a probability of the presence of the microbe above the threshold the sample is further analyzed, and upon determining the sample has a probability of the presence of the microbe below the threshold the sample is not further analyzed.

A first light source transmits about 580 nm light through the sample and a second light source transmits about 800 nm light through the sample, wherein respective instantaneous transmission rates are determined for each wavelength.

The probability is a result of a multiplication of two or more probabilities corresponding to two or more wavelengths, respectively.

According to an embodiment of the present disclosure, a method for testing for presence of a microbe in a sample includes measuring a light wavelength transmission through the sample over time, measuring a change in the light wavelength transmission over time, for biological growth in the sample according to the light wavelength transmission, and determining that the microbe in the sample has a lag phase growth or a log phase growth based on the change in the light wavelength transmission over time, wherein the change in the light wavelength transmission over time is compared to predetermined curves for change in the light wavelength transmission over time corresponding to certain microbes, wherein a concentration of the microbe is known and a species of the microbe is known.

BRIEF DESCRIPTION OF THE DRAWINGS

Preferred embodiments of the present invention will be described below in more detail, with reference to the accompanying drawings.

DETAILED DESCRIPTION OF PREFERRED EMBODIMENTS

Figure 1A:
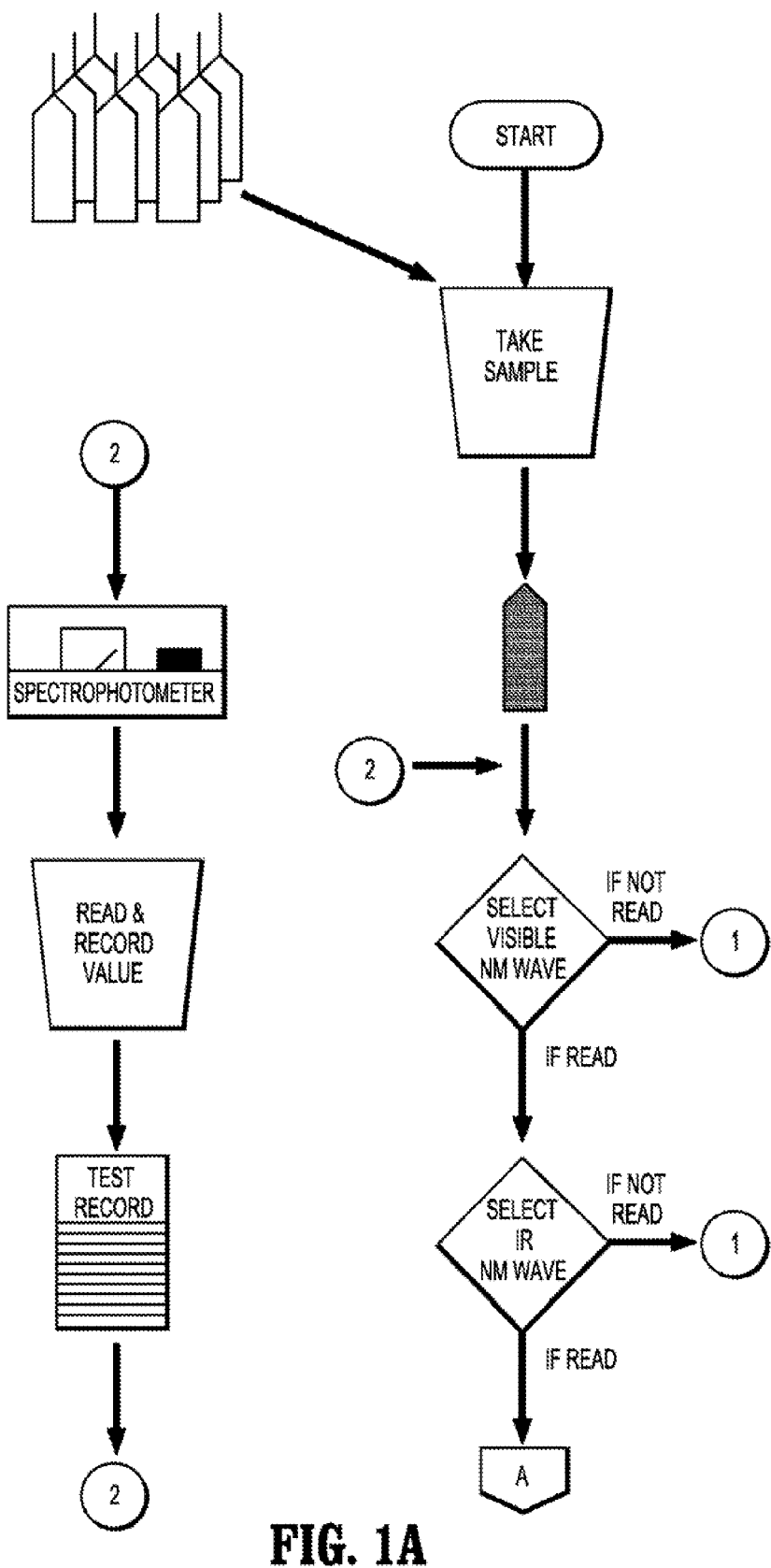
FIGS. 1A-D illustrate a method according to an embodiment of the present disclosure.
Figure 1B:
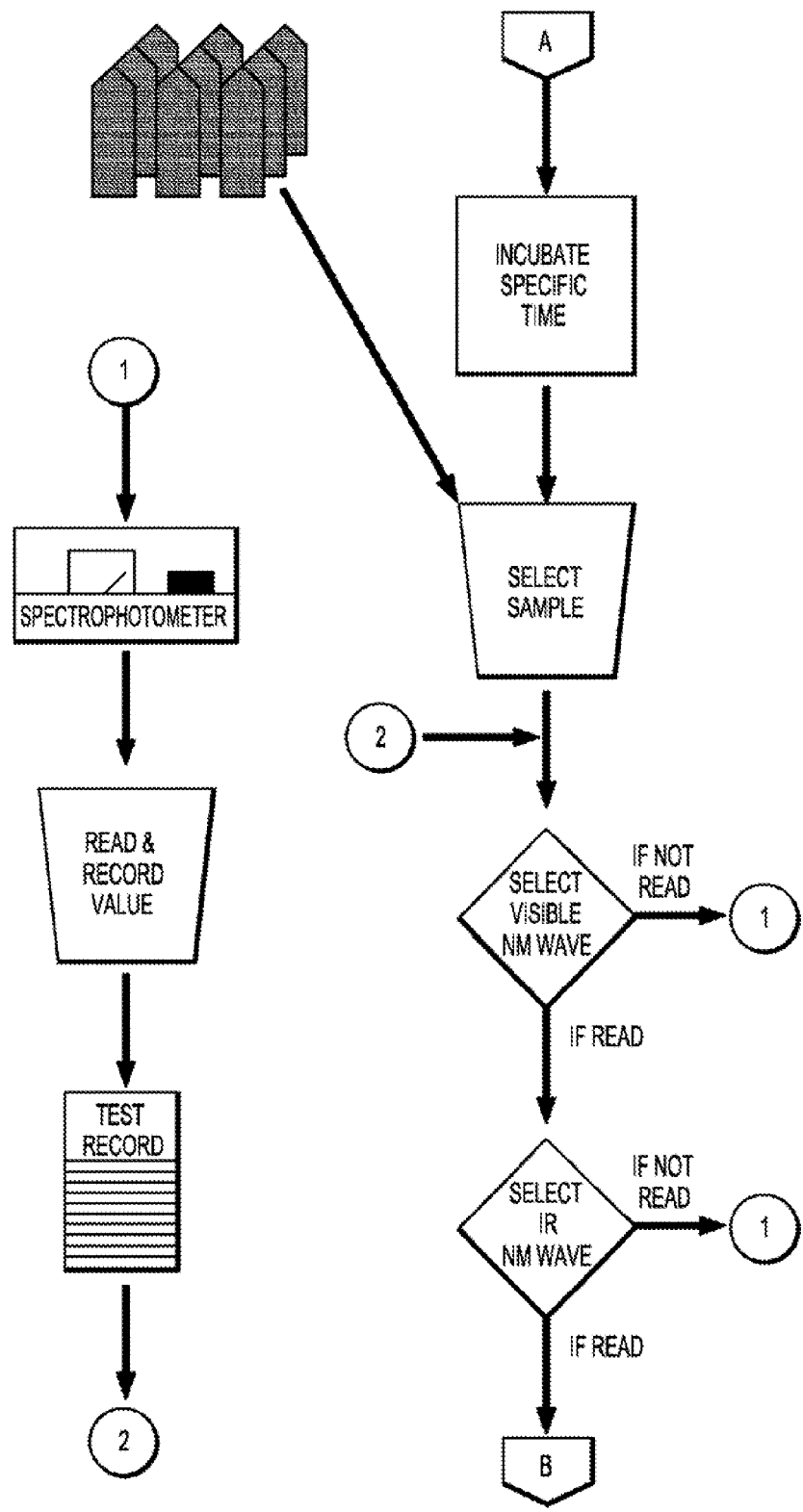
Figure 1C:
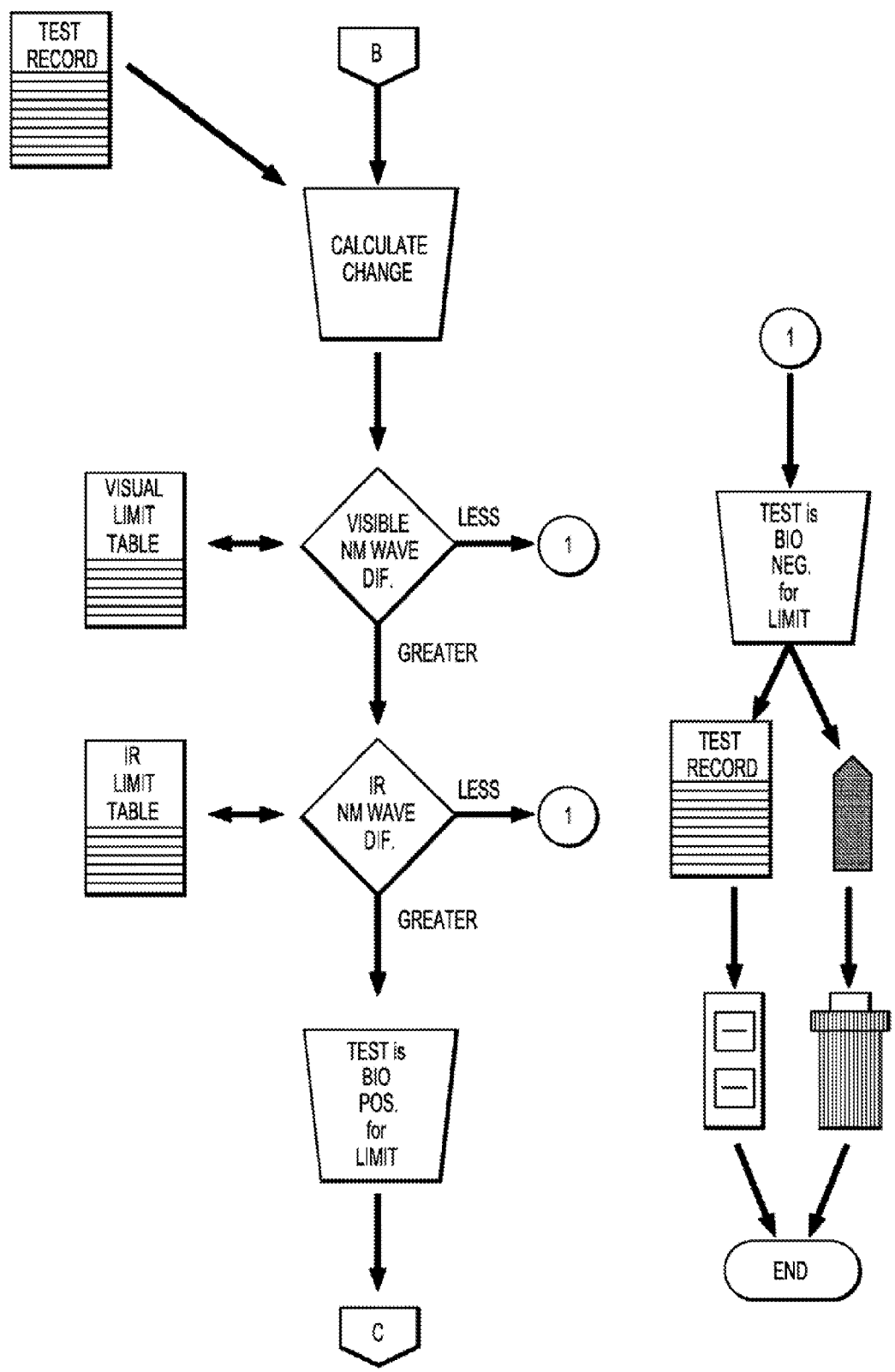
Figure 1D:
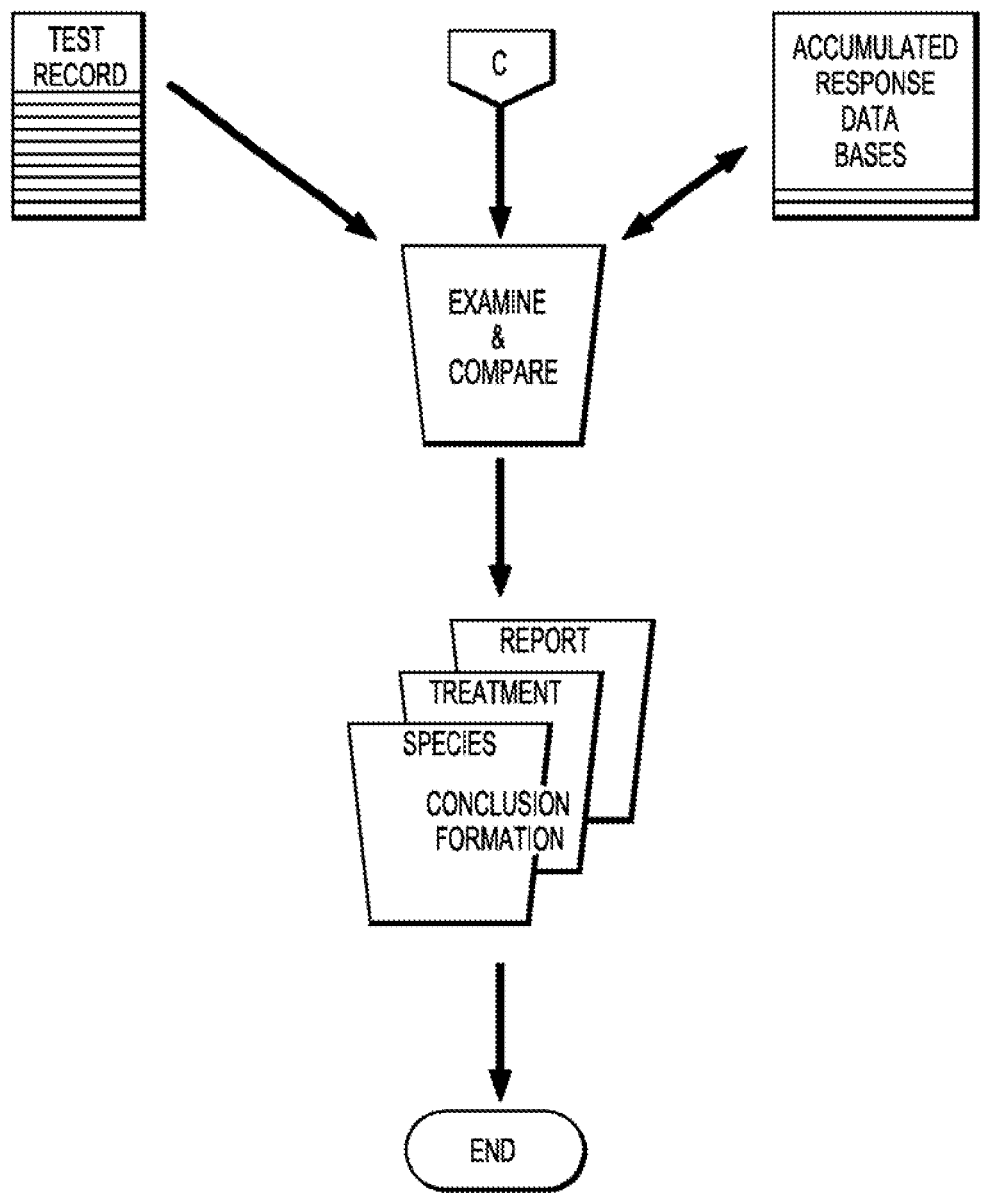
Figure 2A:
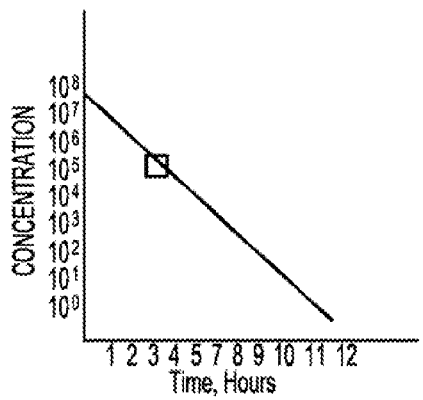
FIGS. 2A-B are graphs showing time to concentration according to an embodiment of the present disclosure.
Figure 2B:
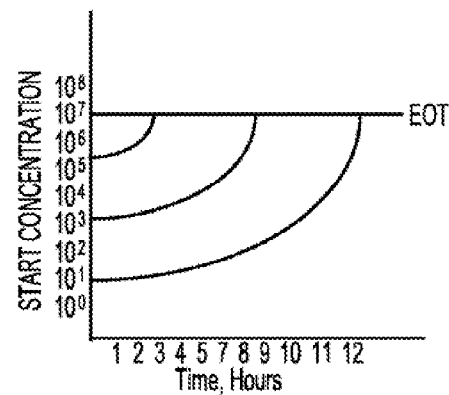
Figure 3A:
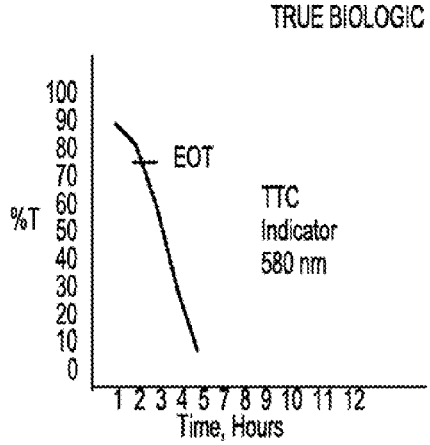
FIGS. 3A-D are graphs showing percent change in transmission rate over time according to an embodiment of the present disclosure.
Figure 3B:
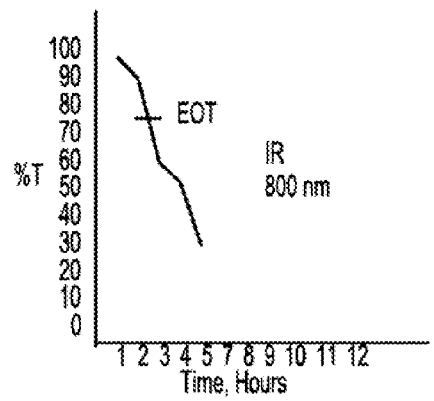
Figure 3C:
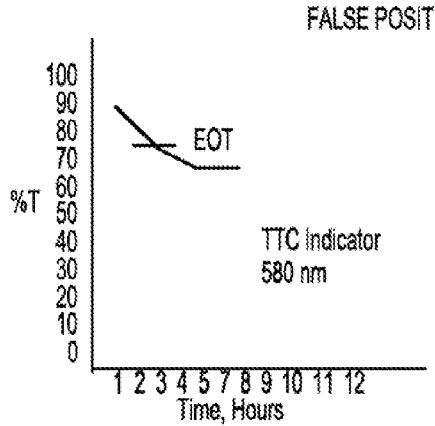
Figure 3D:
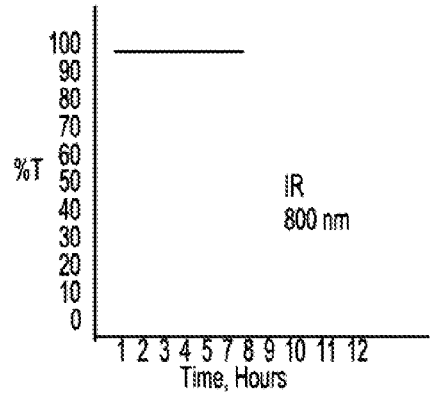

According to an embodiment of the present disclosure, predetermined growth curves for biologic activity may be used in first read determinations (e.g., positive/negative for presence), log/lag phase determinations in time to concentrations analysis, and microbe identification. These growth curves may be determined using an infrared (IR) measurement alone (e.g., FIGS. 3B and 3D) or in combination with different wavelengths of light (e.g., FIGS. 3A and 3C).

Referring to FIGS. 1A-D, a spectrophotometer is used to read and record light transmission through an aqueous sample 101, measures are recorded in a test record 102. The sample is taken 103 and wavelengths are selected for first read analysis 104, 105, these wavelengths for testing are available through the spectrophotometer having different light sources. A determination of potentially positive samples may be made using the first read analysis. The samples, e.g., potential positive samples, may be incubated 106 and a second read 107, 108 is performed for each wavelength of the first read. A change in light transmission through the sample over time is determined 109. For example, if an increase in absorbance and/or a decrease in transmittance in a visible wavelength 110 and an IR wavelength 111 is determined than the sample is confirmed to be positive 112. Negative samples may be determined during the first read analysis 113 and discarded. Further, by comparing the curves for light transmission over time with known curves for a given species (e.g., see FIGS. 2A-B and FIGS. 3A-3D), a species of the sample can be determined.

IR Analysis

According to an embodiment of the present disclosure, biomass can be identified when using common biochemical indicators in an aqueous (e.g., water) assay for bacteria (microbes). Analysis includes illuminating a sample with light having a wavelength of about 800-880 nm over a light path of about 10-90 mm. The length of the light path is relevant to a range of detectable change and a degree of sensitivity. A longer light path corresponds to a decreasing time of detection of microbial growth. When used in concert with visible wavelength biochemical indicators, the possibility of a non-biologic, false positive reaction is substantially reduced.

Known biologic positive samples were analyzed with the IME.TEST™ Total Microbe tester and IME.TEST™ Control Ampoules and a Bausch & Lomb Spec 20 spectrophotometer and tracked on a real time basis. A spectral response of the ampoule sample from 340 nm to 940 nm light demonstrated a desirable response for bacteria growth at a wavelength of about 800 nm. Additional testing demonstrated that the spectral response to about 800 nm light, while strong for bacterial growth was relatively weak (e.g., about 50% slower) when compared to a chemical indicator test response for the same sample. Such a response was unexpected.

Figure 5A:
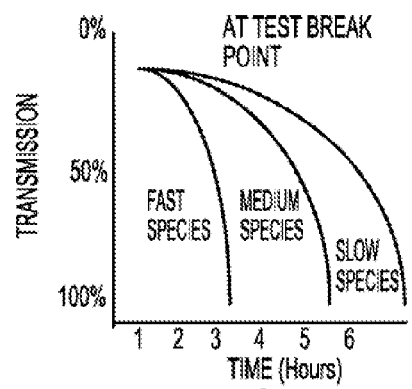
FIGS. 5A-B are graphs showing light transmission rates through a sample over time.
Figure 5B:
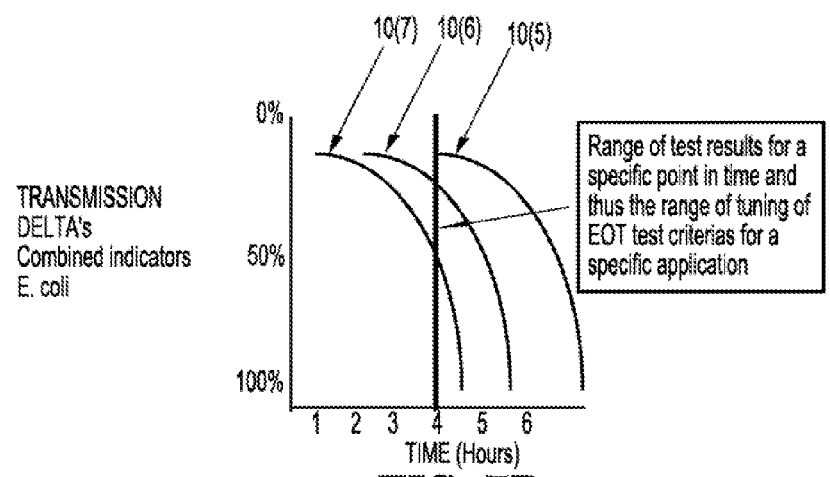
Figure 6:
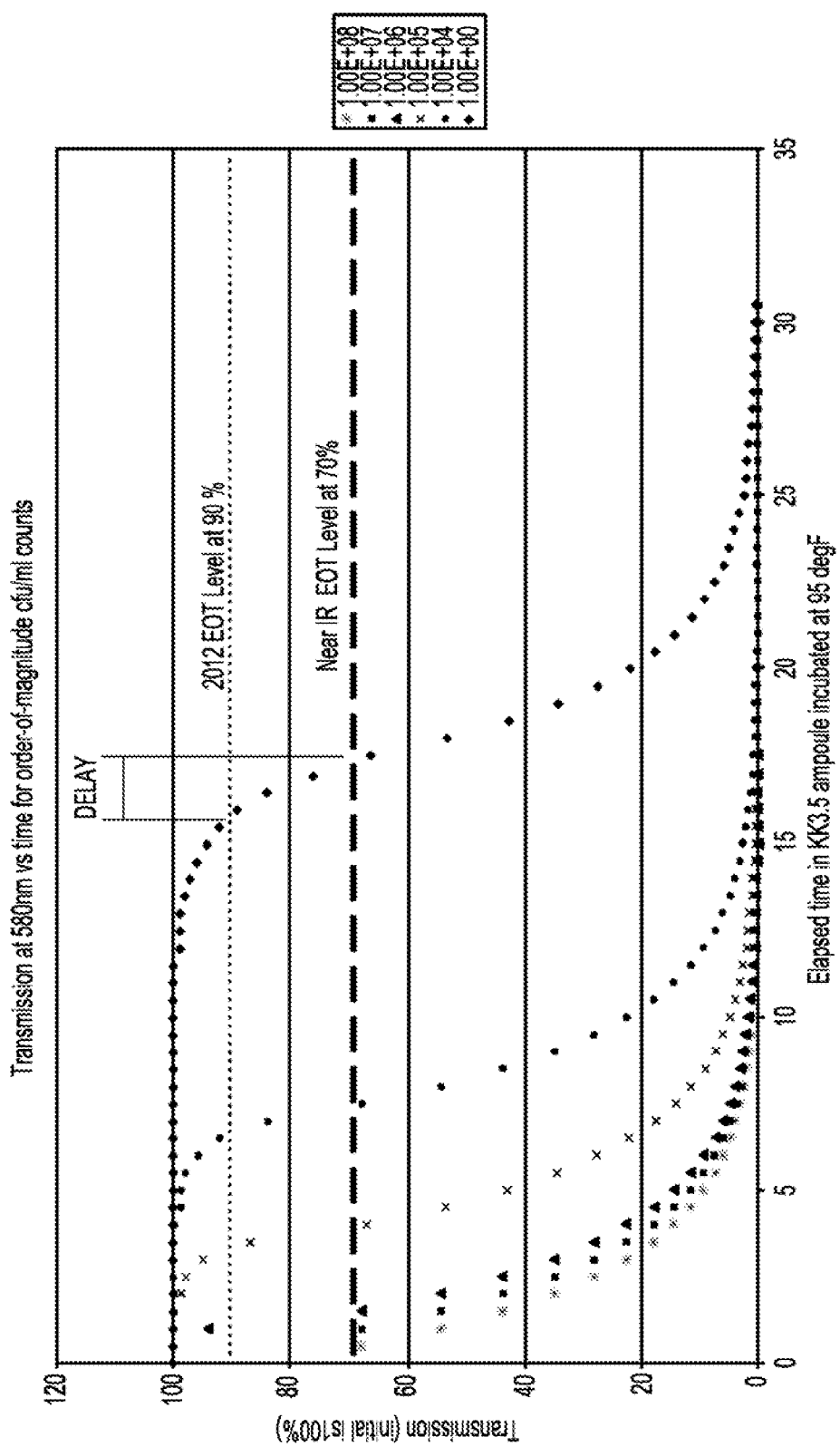
FIG. 6 is a graph of transmission over time according to an embodiment of the present disclosure.

Using light having a wavelength of about 800 nm, test results for the presence of bacteria can be obtained with desirable error rates in competitive time frames without the use of chemical additives. The spectral response is measured as a series of observations over time or a percentage change over time (see FIGS. 3A-D, wherein EOT indicates end of test and FIGS. 5A-B, FIG. 6). A measurement of a change over time enables the sample to be its own standard. No control sample is needed, for example, a sample having a known turbidity or known color.

Figure 4A:
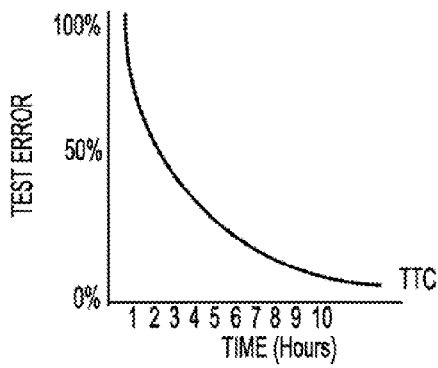
FIGS. 4A-C are graphs showing test error over time according to an embodiment of the present disclosure.
Figure 4B:
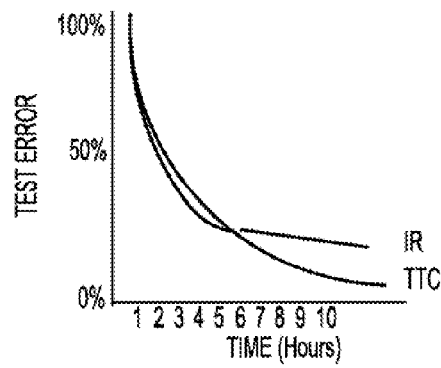
Figure 4C:
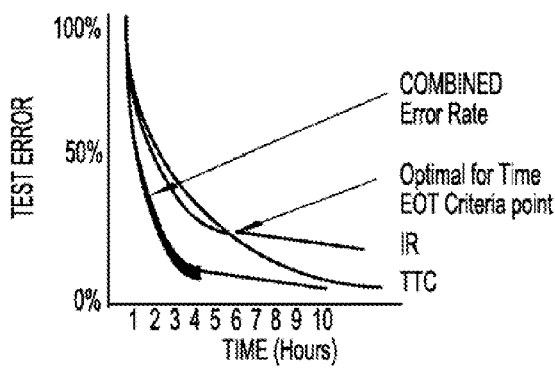

The use of IR wavelengths allows for the tuning of the biologic test to optimize the speed for test results and the reduction of test error induced by chemical, not biologic, conversions of various well-accepted indicators such as TTC. The ~800 nm wavelength, for example, when analyzing *E. coli* (see FIG. 7, percentage of transmission at 800 nm vs. 580 nm), reduces the effects of sample color and turbidity, which may limit a test's ability to perform with visual spectrum indicators. IR is substantially immune to color variations and turbidity. IR includes electromagnetic radiation with wavelengths longer than visible light but shorter than radio waves. Because the measurement includes a change in an IR reading reflected by the microbial growth, even low base line starts can be read for an increase in IR absorbance. The IR absorbance measurement coupled with simultaneous changes in a visual spectral change can increase a probability of accurate bacterial detection and enumeration significantly (e.g., 20% visual error*20% IR error=4% Test error). FIGS. 4A-C demonstrate the combination of two or more testing methods, e.g., visible (TTC curve) and IR light, to achieve statistically reliable detection of microbes. Also, different IR wavelengths may be used for different tests, for example, because of bacteria's varying cell density and size. Further, a single IR wavelength's output signal may change over time with the species of bacteria, for example, as a function of mass of the microbe.

First Read Determination

Figure 13:
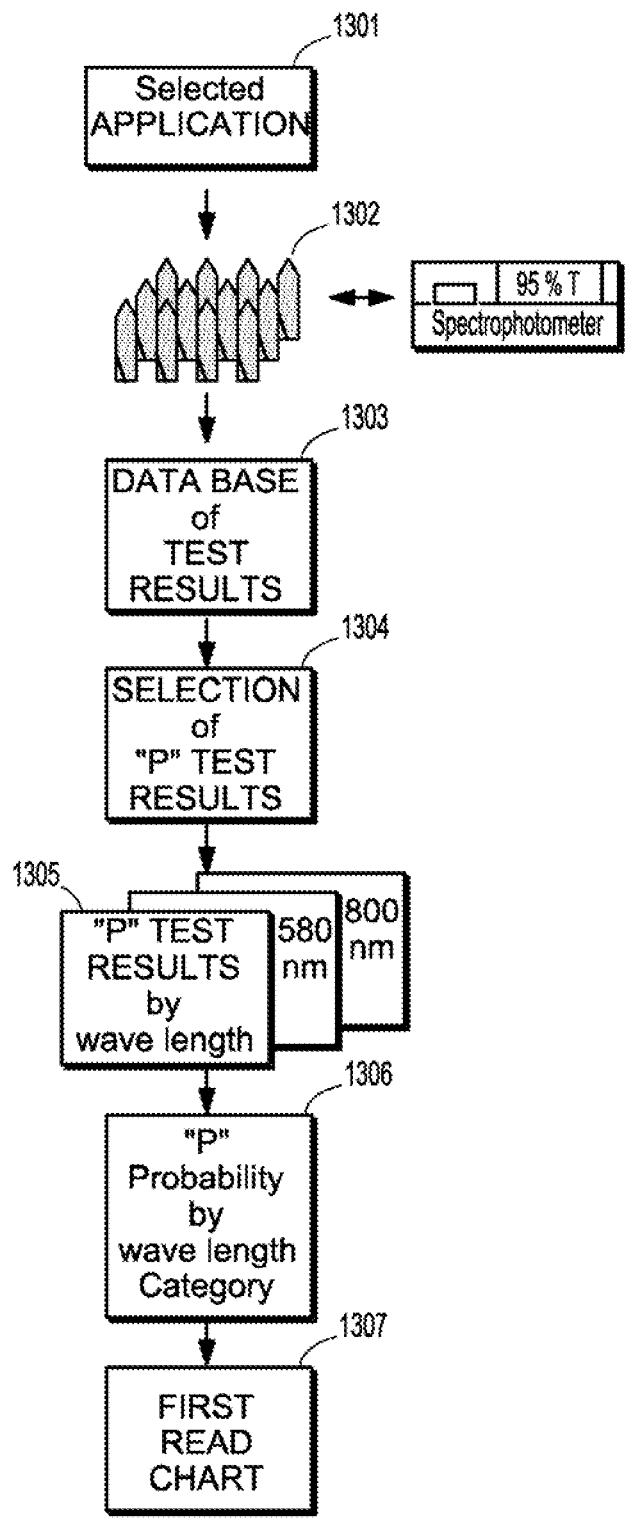
FIG. 13 is a flow chart of a method according to an embodiment of the present disclosure.
Figure 14:
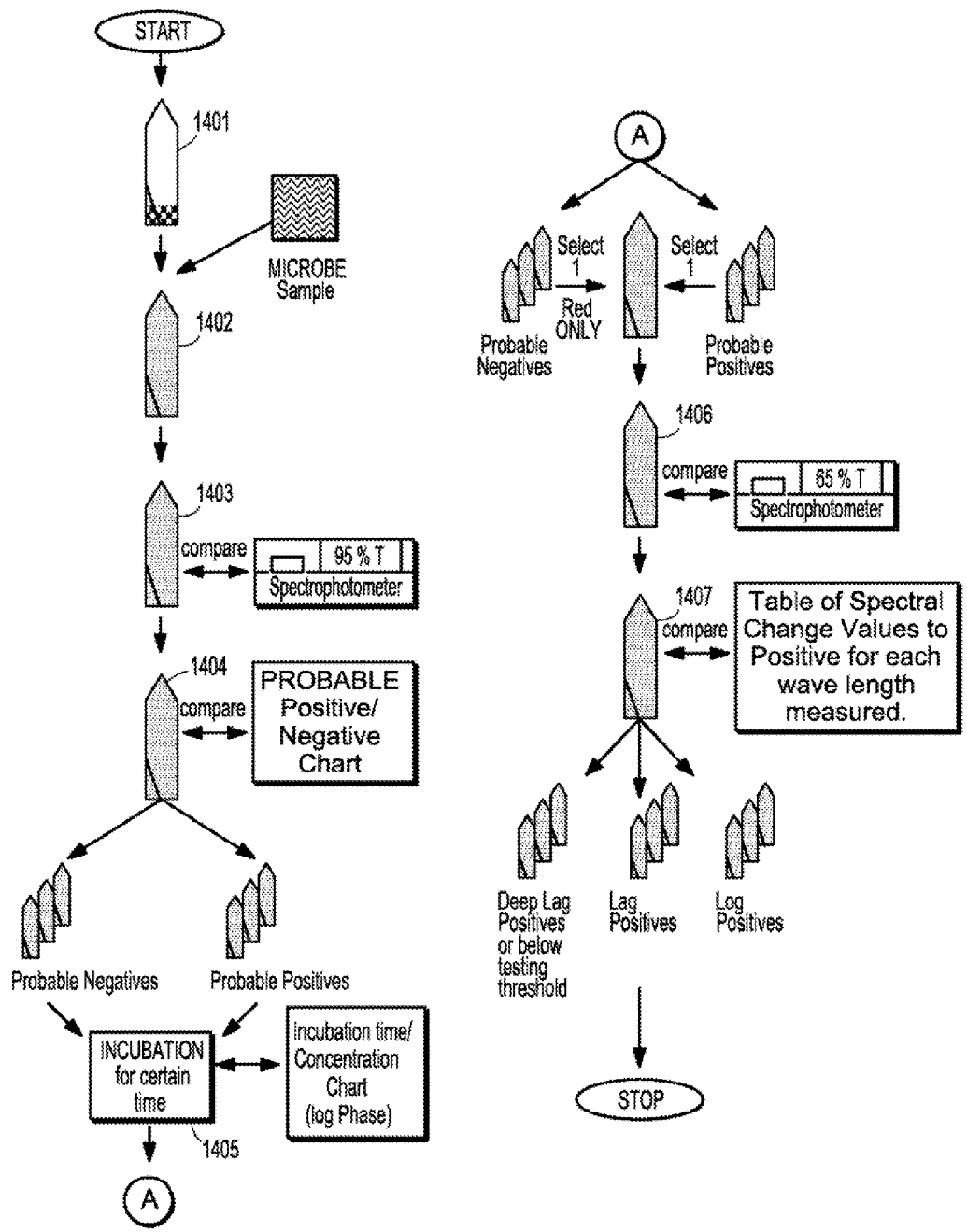
FIG. 14 is a flow chart of a method according to an embodiment of the present disclosure.

Referring to FIGS. 13 and 14, according to an embodiment of the present disclosure, a first read matrix determination may be made upon determining a certain initial profile (e.g., first reading) when examined by various wavelengths of light when the sample is held in a fixed or standardized testing apparatus (e.g., IME.Test™ Control Ampoule and auto analyzer).

Different profiles or growth curves are the result of microbial mass at various concentrations and food refracting selected light wavelengths in a unique way. Multiple sets of light measurements provide a degree of certainty that is statistically significant to make a positive/negative determination for biologic mass at certain thresholds of concentration based upon statistically valid modeling of positive or negative conditions. Additionally, the accumulation of first read values over time will increase the statistical accuracy of the first read projection.

Referring to FIG. 13, an application is selected 1301, e.g., *E. coli* detection. Tests are performed based on the selected application to determine light transmission through the sample over time 1302. The number of tests run can effect the certainty of the data, thus about 500-1000 tests or more are run. The test data, e.g., light transmission curves, are summarized by wavelength, e.g., 580 nm and 800 nm, for a number of observations per a given range of light transmission 1303. Further the number of corresponding positive samples is determined 1304. The test data may be sorted by wavelength and a percentage of positive samples is determined for each range 1305. Based on the ranges, the number of records for each range and the number of positive samples for each range, a table of probabilities is determined 1307; the probability of having a positive sample given an initial reading of a given range 1306. For example, TABLE 1 is an example of a probability table for 580 nm light and a given microbe:

TABLE 1

| RANGE | # OF RECORDS | # OF POSITIVES | PROBABILITY OF POSITIVE |
|---|---|---|---|
| 0-50 | 1 | 0 | 0.0 |
| 51-100 | 7 | 5 | 71.4 |
| 101-150 | 14 | 4 | 28.6 |
| 151-200 | 16 | 2 | 12.5 |
| 201-250 | 32 | 1 | 3.1 |
| 251-300 | 52 | 7 | 13.5 |
| 301-350 | 85 | 4 | 4.7 |
| 351-400 | 124 | 7 | 5.6 |
| 401-450 | 152 | 13 | 8.6 |
| 451-500 | 102 | 5 | 4.9 |
| 501-550 | 102 | 7 | 6.9 |
| 551-600 | 68 | 12 | 17.6 |
| 601-650 | 64 | 17 | 26.6 |
| 651-700 | 51 | 13 | 25.5 |
| 701-750 | 33 | 3 | 9.1 |
| 751-800 | 31 | 10 | 32.3 |
| 801-850 | 34 | 8 | 23.5 |
| 851-900 | 16 | 2 | 12.5 |
| 901-950 | 19 | 3 | 15.8 |
| 951-1000 | 12 | 2 | 16.7 |
| 10001-1021 | 60 | 5 | 8.3 |
| >1021 | 2 | 0 | 0.0 |

Referring to FIG. 14, given the first read tables for each wavelength being observed, a uniform test sample is provided 1401 and a sample, e.g., industrial water or urine, is added to the ampoule 1402. A first reading (e.g., an instantaneous reading determined upon light passing through the sample from a light source to a light detector) is taken for each wavelength 1403. Once the first reading has been spectrally read and compared to a first read chart of predetermined growth curves, it is assigned a probable positive or negative designation 1404. It is important to note that by using two or more wavelengths, statically, the probabilities of having a positive are multiplied, e.g., 26.2% probability for 580 nm*52.4% probability for 800 nm=13.7% probability of positive sample, e.g., sample includes microbe of interest. This initial designation can be as high as about a 90% confidence level.

A confidence level of the probability is affected by the number of observations used to establish the first read chart. A first read chart can constantly be updated by retaining each testing result and periodically redetermining the chart using commonly available PC database and spread sheet products.

Given the determined probabilities and confidences, a user may select first read positives for further analysis, e.g., lag vs. log phase analysis 1404. The positive first read samples may be incubated for additional time 1405. A second reading is taken at the different wavelengths at a later time 1406. Based on the first read and the second read, samples are selected for concentration 1407 and log and lag phase populations may be determined.

A method of determining the microbial concentration level uses the initial reading of two or more optical wavelengths of a microbial sample. The sample needs to be contained in a precise way, which accomplishes the following:
1. Holds the sample in an aqueous matrix;
2. Extracts a fixed sample volume;
3. Provides a precise pre dosage of growth media and selected species indicating chemicals;
4. Maintains a near sterile environment prior to and during use;
5. Can be used in a spectrophotometer or similar piece of equipment capable of reading light transmittance or absorbance at specific wavelengths or range of wavelengths.

These test conditions substantially assure that the only test variation is the sample contents. With these conditions met, a spectrophotometric reading of two or more wavelengths is taken. The wavelengths selected each focus on a different physical aspect such as chemical indicator, UV and/or infrared absorbance/reflectance. When compared to a predetermined chart of probabilities for positive or negative for any set of spectral outputs, the first reading measurement is used to define a probability of positive or negative bacteria presence at a specific threshold of concentration.

The time for taking of the initial reading is important and dependent on the test application. Microbial assessments of high concentration populations will have readings at about 15-30 minutes after exposure to testing media/indicators. Lower level concentration tests have first test readings at longer intervals, about 1-4 hours from test sample exposure to media/indicators.

The resulting probability for positive or negative is then used to set the premise for a log versus lag phase determination. For example a microbial population that is being tested for a $10^6$ log phase microbial concentration level in human urine is first characterized by a study that defines positive or negative percentages for the range of possible readings for each analytical spectral wave length being used (see FIGS. 9-12).

In the field of urine testing for example, one factor in the identification of a true microbial infection of the human urinary system is that a log phase population of microbe species be found in the urine. Urine samples that contain lag phase populations of microbes are considered not urinary tract related and are usually associated with epidermal or normal body discharge from other sources. Because the standard practice of plating urine samples provides no method to identify those populations that are log phase versus those that are lag phase, many urine samples identified as positive urinary tract microbial infections are in fact not positive. By way of example, the standard rule of thumb for the medical professionals is that microbial infections of urinary tract normally represent at any time 10% of the population. However, clinical laboratories typically report 19%-30%+ of urine samples to be microbial positive. The false identification of high concentration contamination as positive microbial infection has serious medical consequence. Such false positive microbial analysis, can cause the improper use of microbial antibiotics, can prolong patient illness and create even more severe medical complications. Additionally, the necessity of identifying log versus lag phase at sampling is important to the proper analysis of samples with a long sitting time before testing (in excess of 7 or 8 hours). Long sit time samples tend to be exposed to significantly different temperatures, nutrient and environmental conditions. Under stress the microbes adapt for survival by shutting down metabolic functions in order to extend their life cycle and return to optimal growth conditions again. Some of these samples would appear to be lag phase when in fact they are not at the time of sampling. The proper judgment of the growth phase of microbial positive samples at sampling is essential for treatment and or control.

It should be noted that the methods described herein are applicable to other types of samples, such as cooling tower or potable water.

A method according to an embodiment of the present disclosure identifies a difference between microbial populations that are in log phase growth versus lag phase growth at the time of sampling. By using a microbial measurement method, which monitors over a specific amount of time, the conversion of a known amount of microbial indicator such as TTC, the phase of microbial growth can be determined, for example, using 580 nm wavelength light. Needed for this growth phase determination are a number of factors. The predetermined factors include a predetermined microbial concentration level to test for and a most probable microbial species present.

Log/Lag Phase Analysis

Test time to concentration values are set using log phase bacteria. Because lag microbes take about 3-7 hours to recover to log phase, a test for log phase can be completed before the lag phase microbes can react. Additionally, the analysis of the beginning section of growth curves reveals that log phase and lag phase bacteria have different curve shapes. This information can then be used to sharpen the time to concentration assessment of unknown samples containing a mix of log and lag phase organisms.

Samples that are designated as probably positive, as determined in a first read analysis, are incubated for a specific period. The specific period for incubation is another predetermined factor. Under controlled laboratory conditions, samples of log phase microbes are placed in the specific sample/media/indicators container. These samples are measured by the selected spectral wavelengths to determine the time such spectral wavelength outputs demonstrate a statistically valid change (see for example, FIGS. 10-12). When all selected wavelengths have demonstrated a change in excess of system background noise, the degree of change is determined for each wavelength at the selected standard time of incubation. For example, a human urine analysis for $10^6$ log phase microbial concentration using 580 nm and 800 nm at 2 hours of incubation is considered positive if the 580 nm drops 10% T (transmission rate) or more and the 800 nm reading drops 20% T or more. With the predetermined spectral change information, the sample is withdrawn from incubation and read spectrophotometrically a second time. The spectral output change is compared to the predetermined values for change to be classified positive or negative.

If all wavelength changes exceed positive threshold values, the sample is considered positive and in the log phase of growth at time of sampling. If all wavelength changes are below the positive threshold values, the sample is considered negative for the threshold being tested and any bacteria present in lag phase. If one or more but all not the positive threshold values have been exceeded, the sample microbial population is considered to be in some more active phase of lag growth but not log phase.

Figure 8:
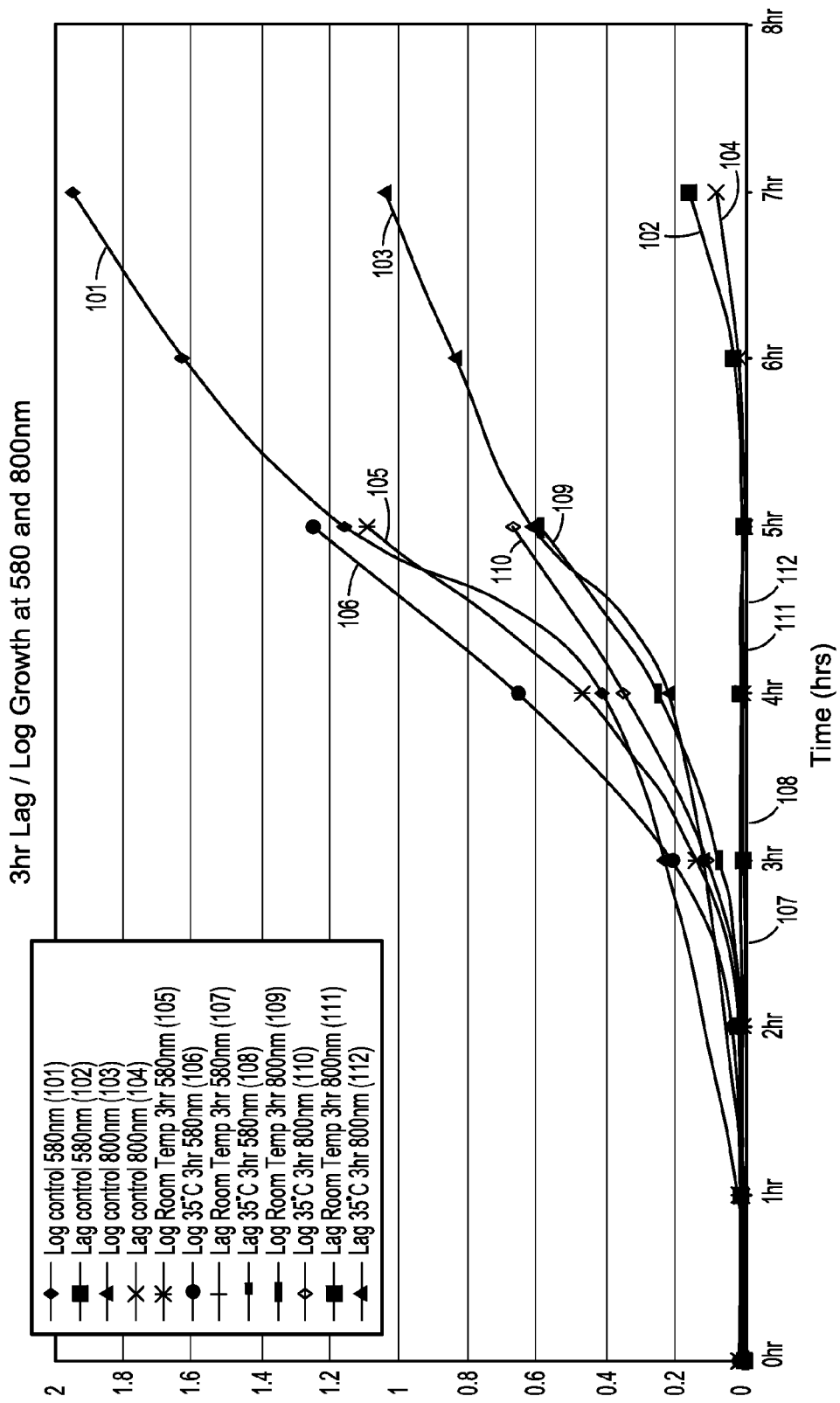
FIG. 8 is a graph of lag and log growth detected in 580 nm and 800 nm light according to an embodiment of the present disclosure.
Figure 10:
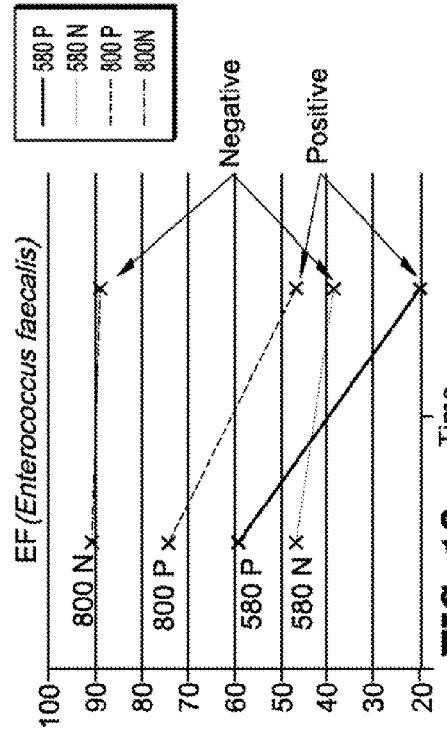
FIG. 10 is a graph illustrating positive and negative curves for the presence of *Enterococcus faecalis* according to an embodiment of the present disclosure.
Figure 12:
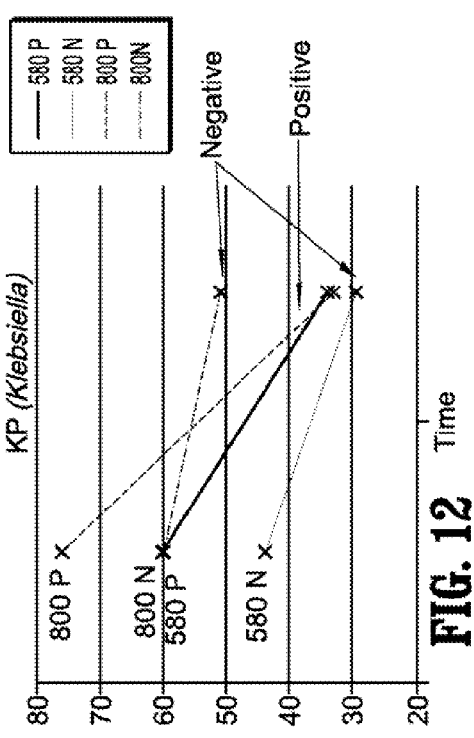
FIG. 12 is a graph illustrating positive and negative curves for the presence of *Klebsiella* according to an embodiment of the present disclosure.
Figure 9:
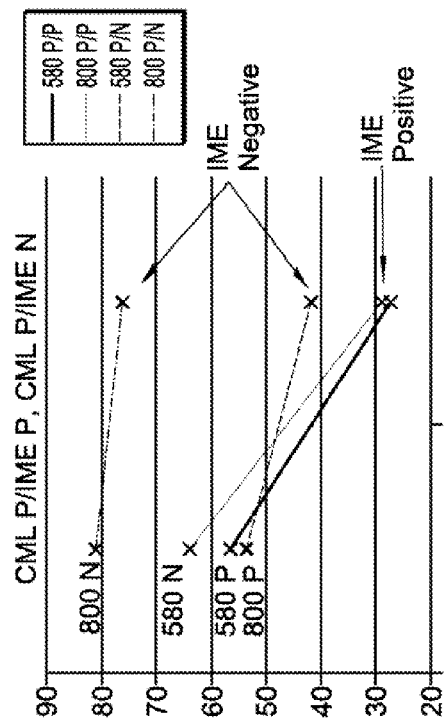
FIG. 9 is a graph comparing positive and negative determinations according to an embodiment of the present disclosure.
Figure 11:
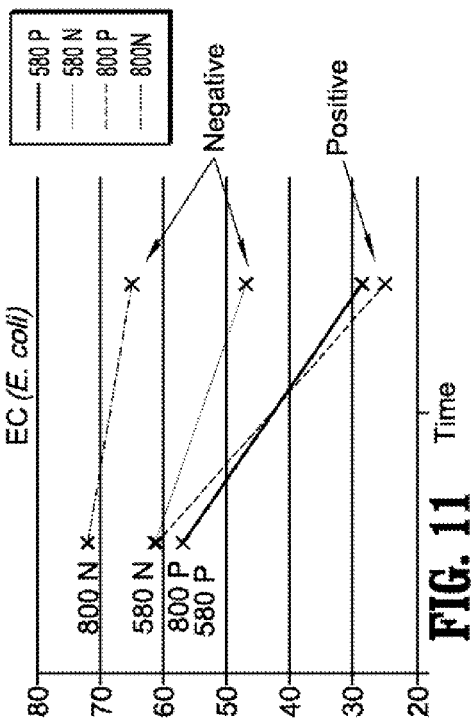
FIG. 11 is a graph illustrating positive and negative curves for the presence of *E. coli* according to an embodiment of the present disclosure.

The degree of lag phase is determined according to the difference between spectral wavelength output change. These growth phase phenomena have been created and observed under laboratory conditions. They have tested and found to be correct for real world testing in human urine and cooling tower water. FIG. 8 provides illustrative results using above-described methods, also shown in FIGS. 13 and 14.

FIG. 8 illustrates the growth of log phase *E. coli* in TSB (tryptic soy broth) with TTC (triphenyltetrazolium chloride crystals) indicator. Curves 801-804 are control curves for 580 nm log and lag and 800 nm log and lag curves, respectively. Growth of *E. coli* was determined with a spectrophotometer at 580 nm and 800 nm over time. A log phase *E. coli* population was recorded as shown as curves 805, 806, 809 and 810. A lag phase *E. coli* population of the same concentration is also shown as 807, 808, 811 and 812. The lag curves 802 and 804 have substantially same shape growth curve as the log curves 801 and 803, but appeared about 4-7 hours later. The difference between the two curves, log and lag, is the recovery time for the lag phase to get to log phase. Microbial growth over time is plotted and the difference between lag and log and start can be determined. Differences in microbe species growth curves can be identified by comparing known curves for species to observed curves to determine a match.

A method according to an embodiment of the present disclosure can use the slope of the various analytical spectral wavelengths to identify microbial species (see Microbe Identification herein). Having the catalog of spectral change by microbial species enhances the ability to determine the degree of lag phase of a microbial population. This is so because a spectral match in the change of slope of each monitored wavelength and relative locus of slope changes for various spectral wavelengths being monitored designates microbial species. Certain changes can also be used to characterize other factors such as chemical environments of the microbes being tested. FIGS. 9-12 demonstrate species identification by spectral wavelength analysis. The charts also demonstrate the difference between log positive microbes and lag negative microbes for the same species.

Such a testing system and method as illustrated in FIGS. 13 and 14 applied to the analysis of human urine for microbial infection can be effectively concluded in about 2-3 hours time with elimination of false positive lag phase microbial populations that may be at the concentration level of positive microbial infection. This method performance is substantially different from the current system of plate analysis, which needs about 24 hours or more and can not distinguish the difference between log versus lag phase growth. This log versus lag phase is a principal determinant for whether a person has a urinary tract microbial infection or not.

Microbe Identification

According to an embodiment of the present disclosure, the plotting of multiple test growth curves simultaneously on the same sample reveals that different species have different shaped curves and relational differences for the various wave lengths used (e.g., 580 & 800 nm).

Figure 7:
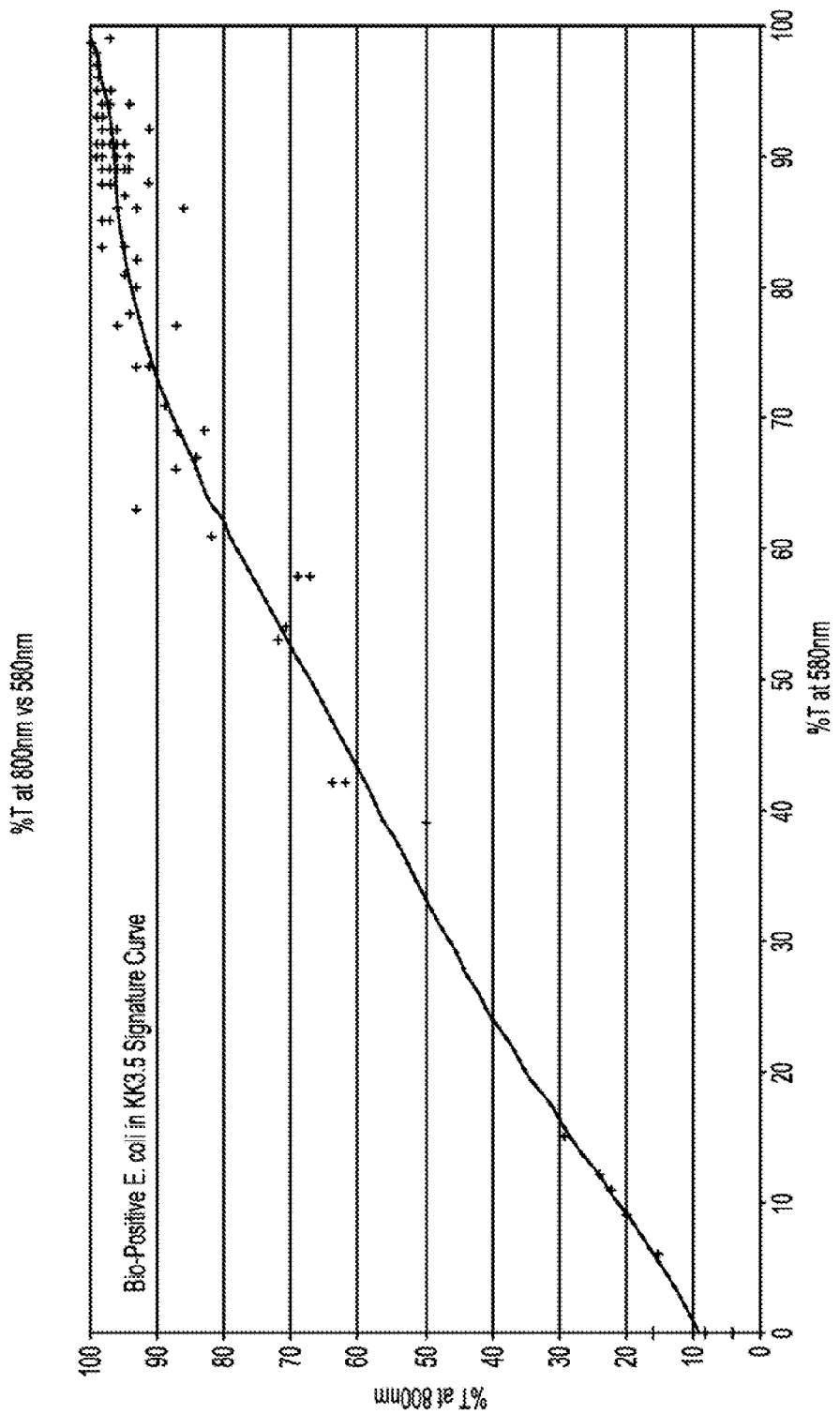
FIG. 7 is a graph showing percent change in transmission rate for two wavelengths according to an embodiment of the present disclosure.

Microbes may be identified according to known behaviors, such as growth patterns measured as a function of light transmission through a sample. The identification may be to, for example, Species. For example, FIG. 7 depicts a signature curve for *E. coli*. Such a curve may be used to identify the presence of *E. coli* in a sample as a function of an observed change in transmission rate over time. Other curves may be provided for different organisms or groups of organisms as demonstrated in FIGS. 9-12.

According to an embodiment of the present disclosure, the system and method may be use a relative change between various light measurements to perform more rapid bacteria species identification. Because the development of a bacterial species by spectral response over time as indicated by a certain wave length and or chemical indicator is unique but not absolute for that species, the use of several indicators will enhance the accuracy of the species identification. For example, *E. coli* species develops at a certain rate per unit of time at a certain concentration level for a selected chemical indicator (e.g., TTC, MUG, ONPG, Indole). If the response over time of the visual wavelength chemical indicator is monitored at specific bacterial concentration levels and this response is measured or compared to IR response, the difference between the two measurements of time to concentration will indicate microbial size and speed of regeneration. This examination needs to be done simultaneously and at controlled incubation temperatures. The combination of speed of bacterial species growth and size as indexed by a study of bacterial growth/IR response makes a strong predictor of bacterial species.

Through the use of specific curve produces a value can be determined that is unique to specific microbes, e.g., species/genius. Particularly when the possible species are limited to a selected group (e.g., 5 or less) such as the analysis of human urine where 4 species represent 96% or better of the likely microbial species present. When predefined and applied to an unknown sample the predominant species can be identified without the presently required secondary testing.

The extension of this knowledge may be used to indicate gram positive and negative conclusions. It is established that IR measurements have been used to predict particle size. Bacteria represent a more difficult challenge because of cell wall thickness variations and other factors associated with the living world but coupled with other spectral measurements including UV and specific knowledge a testing environment, a computerized model can be built that will take what is normally 10-25% of a test result and provide a triangulated result that is quicker and of higher accuracy than a single test analysis.

Embodiments of the present disclosure can demonstrated by the use of the IME.TEST™ Ampoule and IME.TEST™ Auto Incubator/Analyzer or the combined use of a standard laboratory Incubator and spectrophotometer.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

Figure 15:
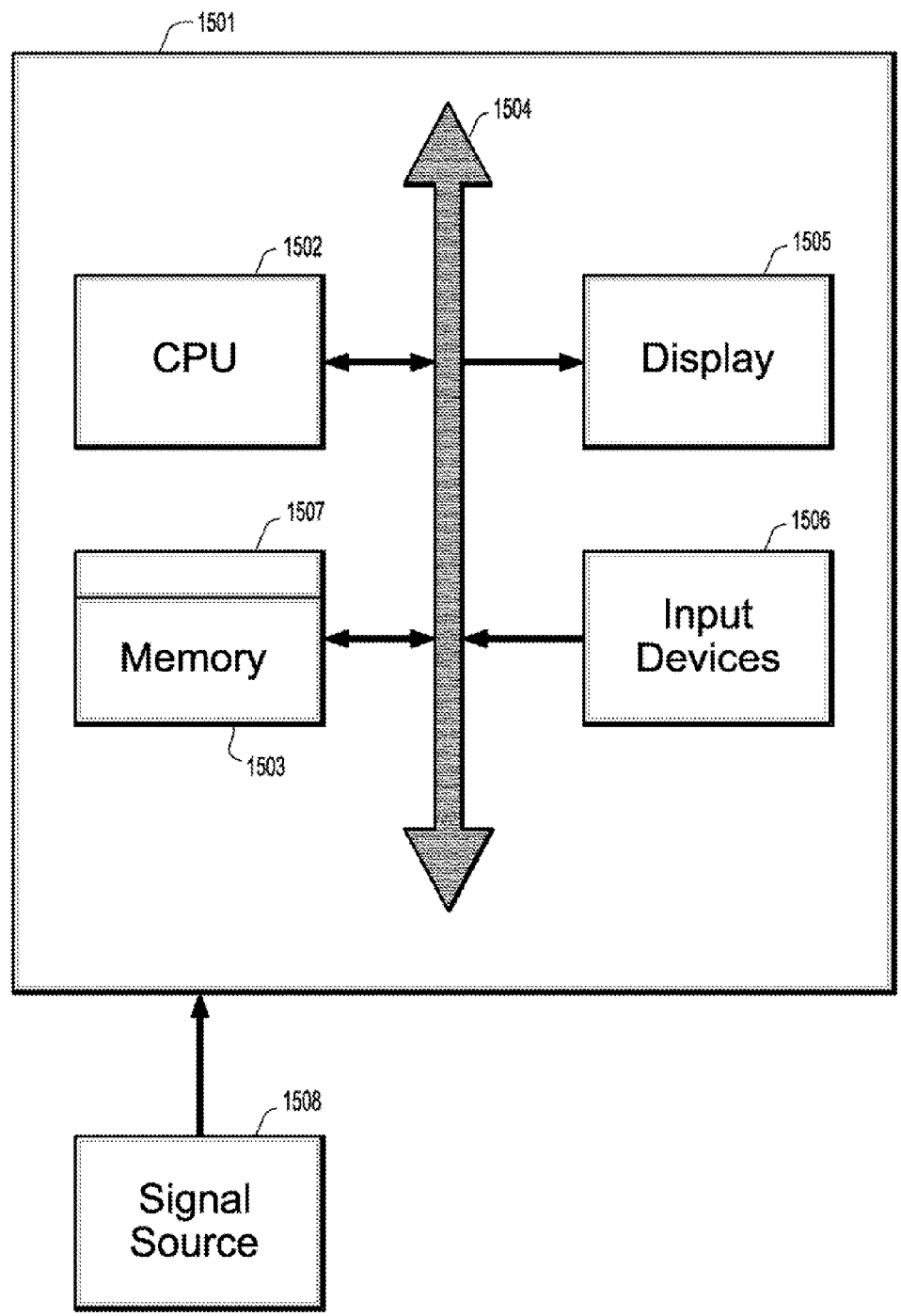
FIG. 15 is a diagram of a system according to an embodiment of the present disclosure.

Referring to FIG. 15, according to an embodiment of the present invention, a computer system 1501 for implementing microbe analysis can comprise, inter alia, a central processing unit (CPU) 1502, a memory 1503 and an input/output (I/O) interface 1504. The computer system 1501 is generally coupled through the I/O interface 1504 to a display 1505 and various input devices 1506 such as a mouse and keyboard. The support circuits can include circuits such as cache, power supplies, clock circuits, and a communications bus. The memory 1503 can include random access memory (RAM), read only memory (ROM), disk drive, tape drive, etc., or a combination thereof. The present invention can be implemented as a routine 1507 that is stored in memory 1503 and executed by the CPU 1502 to process the signal from the signal source 1508. As such, the computer system 1501 is a general-purpose computer system that becomes a specific purpose computer system when executing the routine 1507 of the present invention.

The computer platform 1501 also includes an operating system and microinstruction code. The various processes and functions described herein may either be part of the microinstruction code or part of the application program (or a combination thereof), which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Having described embodiments for a system and method of determining the presence of a biologic agent, it is noted that modifications and variations can be made by persons skilled in the art in light of the above teachings. It is therefore to be understood that changes may be made in the particular embodiments of the invention disclosed which are within the scope and spirit of the invention.

What is claimed is:

1. A method for testing for presence of a microbe in a sample comprising:
   measuring, simultaneously, transmissions of two or more wavelengths of light through the sample over time, wherein the sample functions as its own standard, no control is used, wherein measuring the transmissions comprises;
   determining an elapsed-time for a biological population in the sample to grow from a first concentration to a second concentration, wherein the first and second concentrations are measured using a first of the two or more wavelength transmissions, and the second concentration is a predetermined concentration; and
   measuring a biological mass of the sample during the elapsed-time using a second of the two or more wavelength transmissions; and
   determining the presence of the microbe based on a combination of the first and second concentrations and the biological mass given the elapsed-time.

2. The method of claim 1, wherein an infrared wavelength is used to measure the biological mass of the sample and a visible wavelength is used to measure the first and second concentrations of the biological population.

3. The method of claim 1, further comprising:
   comparing a change in transmission rate for each of the two or more wavelengths over time to a catalog of spectral change ending at a time the predetermined concentration is measured; and
   determining a species of the microbe by matching the change of slope of each monitored wavelength and relative locus of slope changes for various spectral wavelengths being monitored with a predetermined change of slope and relative locus of slope changes for the various spectral wavelengths for the species.

4. The method of claim 1, further comprising determining that the microbe in the sample has a lag phase growth or a log phase growth based on a change in the comparison over time up to a time the predetermined concentration is measured.

5. A method for testing for presence of a microbe in a sample comprising:
   measuring an instantaneous transmission rate of two or more wavelengths through the sample, a first wavelength corresponding to a concentration measurement of the microbe and a second wavelength corresponding to a mass measurement of the microbe;
   providing predetermined transmission rates corresponding to positive or negative samples for the presence of the microbe for each of the two or more wavelengths; and
   determining a probability of the presence of the microbe based on the instantaneous transmission rate for each of the two or more wavelengths through the sample up to the predetermined concentration by comparing the instantaneous transmission rates to the predetermined transmission rates and an elapsed time to achieve the predetermined concentration, wherein the probability is a result of a multiplication of two or more probabilities corresponding to two or more wavelengths, respectively.

6. The method of claim 5, wherein each of the predetermined transmission rates is associated with a known confidence level.

7. The method of claim 5, wherein the probability of the presence of the microbe is compared to a predetermined threshold, wherein upon determining the sample has a probability of the presence of the microbe above the threshold the sample is further analyzed, and upon determining the sample has a probability of the presence of the microbe below the threshold the sample is not further analyzed.

8. The method of claim 5, wherein a first light source transmits about 580 nm light through the sample and a second light source transmits about 800 nm light through the sample, wherein respective instantaneous transmission rates are determined for each wavelength.

9. The method of claim 5, further comprising determining that the microbe in the sample has a lag phase growth or a log phase growth based on a change in the comparison over time up to a time the predetermined concentration is measured.

* * * * *